US008933275B2

(12) United States Patent
Bricker et al.

(10) Patent No.: US 8,933,275 B2
(45) Date of Patent: Jan. 13, 2015

(54) PRODUCTION OF OXYGENATES FROM A METHANE CONVERSION PROCESS

(71) Applicant: UOP LLC, Des Plaines, IL (US)

(72) Inventors: Jeffery C. Bricker, Buffalo Grove, IL (US); John Q. Chen, Glenview, IL (US); Peter K. Coughlin, Mundelein, IL (US)

(73) Assignee: UOP LLC, Des Plaines, IL (US)

(*) Notice: Subject to any disclaimer, the term of this patent is extended or adjusted under 35 U.S.C. 154(b) by 0 days.

(21) Appl. No.: 13/915,099

(22) Filed: Jun. 11, 2013

(65) Prior Publication Data

US 2014/0058135 A1 Feb. 27, 2014

Related U.S. Application Data

(60) Provisional application No. 61/691,368, filed on Aug. 21, 2012.

(51) Int. Cl.
*C07C 45/26* (2006.01)
*C07C 41/05* (2006.01)
*C07C 29/44* (2006.01)
*B01J 19/10* (2006.01)
*C07C 45/50* (2006.01)
*C07C 45/34* (2006.01)
*C07B 41/02* (2006.01)
*C07B 41/04* (2006.01)
*C07C 2/82* (2006.01)
*C07C 29/04* (2006.01)
*C07C 5/09* (2006.01)

(52) U.S. Cl.
CPC .................. *B01J 19/10* (2013.01); *C07C 45/50* (2013.01); *C07C 45/34* (2013.01); *C07B 41/02* (2013.01); *C07C 29/44* (2013.01); *C07C 41/05* (2013.01); *C07C 45/26* (2013.01); *C07B 41/04* (2013.01); *C07C 2/82* (2013.01); *C07C 29/04* (2013.01); *C07C 5/09* (2013.01)
USPC ........................... 568/451; 568/691; 568/909

(58) Field of Classification Search
USPC ......................................... 568/401, 691, 909
See application file for complete search history.

(56) References Cited

U.S. PATENT DOCUMENTS

| | | |
|---|---|---|
| 748,091 A | 12/1903 | Nethery |
| 2,581,102 A | 1/1952 | Hodges |
| 2,822,410 A | 2/1958 | Wojcik et al. |
| 3,565,940 A | 2/1971 | Brown et al. |
| 3,615,164 A | 10/1971 | Baker et al. |
| 3,816,975 A | 6/1974 | Collins |
| 4,009,219 A | 2/1977 | Tamers |
| 4,094,777 A | 6/1978 | Sugier et al. |
| 4,136,015 A | 1/1979 | Kamm et al. |
| 4,181,662 A | 1/1980 | Sweeney |
| 4,191,636 A | 3/1980 | Fukui et al. |
| 4,288,641 A | 9/1981 | Codignola et al. |
| 4,356,124 A | 10/1982 | Pesa et al. |
| 4,357,228 A | 11/1982 | Che |
| 4,387,263 A | 6/1983 | Vogt et al. |
| 4,426,248 A | 1/1984 | Jackson |
| 4,493,715 A | 1/1985 | Hogan et al. |
| 4,544,792 A | 10/1985 | Smith et al. |
| 4,587,373 A | 5/1986 | Hsia |
| 4,724,272 A | 2/1988 | Raniere et al. |
| 4,744,221 A | 5/1988 | Knollmueller |
| 4,892,567 A | 1/1990 | Yan |
| 4,929,789 A | 5/1990 | Gupta et al. |
| 5,026,935 A | 6/1991 | Leyshon et al. |
| 5,095,163 A | 3/1992 | Barger |
| 5,096,470 A | 3/1992 | Krishnamurthy |
| 5,126,308 A | 6/1992 | Barger et al. |
| 5,191,141 A | 3/1993 | Barger et al. |
| 5,219,530 A | 6/1993 | Hertzberg et al. |
| 5,227,570 A | 7/1993 | Tan |
| 5,232,474 A | 8/1993 | Jain |
| 5,276,257 A | 1/1994 | Diesen |
| 5,278,344 A | 1/1994 | Gosling et al. |
| 5,300,216 A | 4/1994 | Hertzberg et al. |
| 5,419,884 A | 5/1995 | Weekman et al. |
| 5,446,232 A | 8/1995 | Chen et al. |
| 5,478,950 A | 12/1995 | Bergfeld et al. |
| 5,482,616 A | 1/1996 | Brahma et al. |
| 5,510,565 A | 4/1996 | Tan et al. |
| 5,760,266 A | 6/1998 | Eaton et al. |
| 5,990,372 A | 11/1999 | Blankenship et al. |
| 6,049,011 A | 4/2000 | Kiss et al. |

(Continued)

FOREIGN PATENT DOCUMENTS

| | | |
|---|---|---|
| BY | 7932 C1 | 4/2006 |
| CA | 2391441 A1 | 6/2001 |
| CN | 101928217 A | 12/2010 |
| CN | 201768561 U1 | 3/2011 |
| CN | 102247876 A | 11/2011 |
| DE | 3327000 A1 | 2/1985 |
| DE | 19626484 A1 | 1/1998 |
| DE | 10252859 A1 | 5/2004 |
| EA | 008761 B1 | 8/2007 |
| EA | 200800261 A1 | 4/2008 |

(Continued)

OTHER PUBLICATIONS

Abedi, "Economic Analysis of a New Gas Ethylene Technology", Thesis—Texas A&M University, May 2007.
Anvari, "Enhancement of 2,3-Butanediol Production by *Klebsiella oxytoca* PTCC 1402", Journal of Biomedicine and Biotechnology, 2011.
Argonne National Laboratory, "Novel Membrane Technology for Green Ethylene Production", Dept of Energy, Energy Innovation Portal.
Barnard, "The pyrolysis of tert.-butanol", Trans. Faraday Soc., 1959, vol. 55, pp. 947-951.

(Continued)

*Primary Examiner* — Sikarl Witherspoon

(57) ABSTRACT

Methods and systems are provided for converting methane in a feed stream to acetylene. The method includes processing acetylene as an intermediate stream to form a stream having oxygenates. The hydrocarbon stream is introduced into a supersonic reactor and pyrolyzed to convert at least a portion of the methane to acetylene. The reactor effluent stream may be treated to convert acetylene to oxygenates through subsequent reactors.

24 Claims, 2 Drawing Sheets

(56) References Cited

U.S. PATENT DOCUMENTS

| | | |
|---|---|---|
| 6,190,623 B1 | 2/2001 | Sanger et al. |
| 6,210,791 B1 | 4/2001 | Skoog et al. |
| 6,278,033 B1 | 8/2001 | Flick et al. |
| 6,395,197 B1 | 5/2002 | Detering et al. |
| 6,442,931 B1 | 9/2002 | Vasin et al. |
| 6,443,354 B1 | 9/2002 | Plochl et al. |
| 6,465,701 B1 | 10/2002 | Marsella et al. |
| 6,478,535 B1 | 11/2002 | Chung et al. |
| 6,610,124 B1 | 8/2003 | Dolan et al. |
| 6,688,100 B1 | 2/2004 | Wherley et al. |
| 6,695,077 B2 | 2/2004 | Szymocha et al. |
| 6,761,777 B1 | 7/2004 | Radon |
| 6,764,602 B2 | 7/2004 | Shutt et al. |
| 6,821,500 B2 | 11/2004 | Fincke et al. |
| 6,953,867 B2 | 10/2005 | Cockman et al. |
| 6,962,199 B1 | 11/2005 | Tjeenk Willink |
| 7,000,306 B2 | 2/2006 | Rice et al. |
| 7,045,670 B2 | 5/2006 | Johnson et al. |
| 7,183,451 B2 | 2/2007 | Gattis et al. |
| 7,208,647 B2 | 4/2007 | Peterson et al. |
| 7,211,128 B2 | 5/2007 | Thomas et al. |
| 7,253,328 B2 | 8/2007 | Stauffer |
| 7,442,350 B1 | 10/2008 | Vanden Bussche |
| 7,655,135 B2 | 2/2010 | Havlik et al. |
| 7,667,085 B2 | 2/2010 | Gattis et al. |
| 7,692,051 B2 | 4/2010 | Johnson et al. |
| 7,744,763 B2 | 6/2010 | Cross et al. |
| 7,759,288 B2 | 7/2010 | Prichett et al. |
| 7,759,531 B2 | 7/2010 | Pinkos et al. |
| 7,763,163 B2 | 7/2010 | Koseoglu |
| 7,901,486 B2 | 3/2011 | Cross et al. |
| 7,915,461 B2 | 3/2011 | Gattis et al. |
| 7,915,462 B2 | 3/2011 | Gattis et al. |
| 7,915,463 B2 | 3/2011 | Gattis et al. |
| 7,915,464 B2 | 3/2011 | Gattis et al. |
| 7,915,465 B2 | 3/2011 | Gattis et al. |
| 7,915,466 B2 | 3/2011 | Gattis et al. |
| 7,919,431 B2 | 4/2011 | Johnson et al. |
| 8,013,196 B2 | 9/2011 | Mamedov et al. |
| 8,013,197 B2 | 9/2011 | Peterson et al. |
| 8,080,697 B2 | 12/2011 | Lin et al. |
| 8,088,962 B2 | 1/2012 | Klanner et al. |
| 8,137,476 B2 | 3/2012 | Morrow et al. |
| 8,211,312 B2 | 7/2012 | Stewart et al. |
| 2002/0154741 A1 | 10/2002 | Rigali et al. |
| 2004/0079228 A1 | 4/2004 | Wijmans et al. |
| 2005/0070748 A1 | 3/2005 | Ellis et al. |
| 2006/0283780 A1 | 12/2006 | Spivey et al. |
| 2007/0018038 A1 | 1/2007 | Jarmon et al. |
| 2007/0149807 A1 | 6/2007 | Dieterle et al. |
| 2007/0191664 A1 | 8/2007 | Hershkowitz et al. |
| 2009/0042998 A1 | 2/2009 | Hashimoto et al. |
| 2010/0005963 A1 | 1/2010 | Snape et al. |
| 2010/0044626 A1 | 2/2010 | Fischer et al. |
| 2010/0126909 A1 | 5/2010 | Bhasin et al. |
| 2010/0130803 A1 | 5/2010 | Keusenkothen et al. |
| 2010/0228069 A1 | 9/2010 | Kuznicki et al. |
| 2010/0319536 A1 | 12/2010 | Song et al. |
| 2011/0071331 A1 | 3/2011 | Basset et al. |
| 2011/0094378 A1 | 4/2011 | Mitariten |
| 2011/0114285 A1 | 5/2011 | Buxbaum |
| 2011/0297269 A1 | 12/2011 | Pilon et al. |
| 2012/0029257 A1 | 2/2012 | Chen et al. |
| 2012/0178833 A1 | 7/2012 | Clomburg, Jr. et al. |

FOREIGN PATENT DOCUMENTS

| | | |
|---|---|---|
| EA | 013242 B1 | 4/2010 |
| EP | 0039918 A1 | 11/1981 |
| EP | 011707 B1 | 9/1982 |
| EP | 0158863 A2 | 10/1985 |
| EP | 0173501 A2 | 3/1986 |
| EP | 0263259 A2 | 4/1988 |
| EP | 1677910 A2 | 3/2005 |
| EP | 1667949 A2 | 4/2005 |
| EP | 1678274 A2 | 4/2005 |
| EP | 1856047 A2 | 8/2006 |
| EP | 2022772 A1 | 2/2009 |
| EP | 2224025 A1 | 9/2010 |
| EP | 2417721 A1 | 10/2010 |
| EP | 1663918 B1 | 2/2012 |
| EP | 2049456 B1 | 3/2012 |
| GB | 283163 A | 1/1929 |
| GB | 332258 A | 7/1930 |
| GB | 334193 A | 8/1930 |
| GB | 451794 A | 8/1936 |
| GB | 1358862 A | 7/1974 |
| GB | 2000180 A | 4/1979 |
| GB | 2220674 A | 1/1990 |
| JP | 6046976 A | 3/1985 |
| JP | 60129552 A | 7/1985 |
| JP | 1132535 A | 5/1989 |
| JP | 01277196 A | 11/1989 |
| JP | 2002348580 A | 12/2002 |
| KR | 2002009748 A | 2/2002 |
| RU | 2065866 C1 | 8/1996 |
| RU | 2145952 C1 | 2/2000 |
| RU | 98101950 A | 2/2000 |
| RU | 2158747 C1 | 11/2000 |
| RU | 2170617 C2 | 7/2001 |
| RU | 2187768 C2 | 8/2002 |
| RU | 2204434 C2 | 5/2003 |
| RU | 2222569 C2 | 1/2004 |
| RU | 2261995 C2 | 10/2005 |
| RU | 2264855 C2 | 11/2005 |
| RU | 2346737 C2 | 2/2009 |
| RU | 2363521 C1 | 8/2009 |
| RU | 2367668 C2 | 9/2009 |
| RU | 2373178 C2 | 11/2009 |
| RU | 2427608 C2 | 8/2011 |
| RU | 2438083 C2 | 12/2011 |
| RU | 2440962 C1 | 1/2012 |
| RU | 2443758 C2 | 2/2012 |
| RU | 116365 U1 | 5/2012 |
| RU | 2451658 C2 | 5/2012 |
| SU | 234422 A1 | 5/1969 |
| SU | 280739 A1 | 2/1976 |
| SU | 803969 A | 2/1981 |
| SU | 392723 A | 7/1983 |
| SU | 410596 A | 7/1983 |
| SU | 1613481 A1 | 12/1990 |
| SU | 1776652 A1 | 11/1992 |
| SU | 1778146 A1 | 11/1992 |
| WO | 9109829 A1 | 7/1991 |
| WO | 9518089 A1 | 7/1995 |
| WO | 9602792 A2 | 2/1996 |
| WO | 02058818 A2 | 8/2002 |
| WO | 03083015 A2 | 10/2003 |
| WO | 2004074220 A1 | 9/2004 |
| WO | 2009080621 A1 | 7/2009 |
| WO | 2009121456 A1 | 10/2009 |
| WO | 2010066281 A1 | 6/2010 |
| WO | 2010079177 A2 | 7/2010 |
| WO | 2010127752 A1 | 11/2010 |
| WO | 2011021024 A1 | 2/2011 |
| WO | 2011081836 A2 | 7/2011 |
| WO | 2011090616 A2 | 7/2011 |
| WO | 2012005862 A1 | 1/2012 |
| WO | 2012108686 A2 | 8/2012 |

OTHER PUBLICATIONS

Bartholome, "The BASF-process for production of acetylene by partial oxidation of gaseous hydrocarbons", Special Supplement to Chemical Engineering Science, 1954, pp. 94-104. vol. 3.

Bergeot, Simulated moving bed reactor paraxylene production, Chemical Engineering Transactions, 2009, pp. 87-92, vol. 17.

Besev, "Radical Cyclization Approaches to Pyrrolidines", Acta Universitatis Upsaliensis, Uppsala University, 2002.

Biswas, "Enhanced production of 2,3-Butanediol by engineered *Bacillus subtillis*", Appl. Microbiol. Biotechnology, 2012, vol. 94, pp. 651-658.

Buhl, "Bio-Production of Light Olefins", ChemManager online, Europe, Mar. 19, 2012.

(56) References Cited

OTHER PUBLICATIONS

Cerff, "Supersonic Injection and Mixing in the Shock Wave Reactor", Thesis M.S. Aeronatuics and Astronautics, University of Washington, 2010.
Chempedia, "Alternative Manufacturing Process of ⌊-Caprolactam", LookChem.com.
Chempedia, "Hydrodealkylation of toulene", LookChem.com.
Chempedia, "Manufacture of 1,2-Butanediol", LookChem.com.
Chempedia, "Production of Vinyl Chloride from Ethylene", Lookchem.com.
Chemsystems, "1,4-Butanediol/THF 98/99S1", Sep. 1999.
Chemsystems, "Acetylene Production Technologies Perp 05/06S9", Nexant, 2007.
Chemsystems, "Acrylic Acid Perp 08/09", Nexant Aug. 2010.
Chemsystems, "Butadiene/Butylenes Perp 09/10-5", Nexant, Sep. 2010.
Chemsystems online, "Ethylene oxide/Ethylene Glycol", Nexant, 2009.
Chemsystems, "Green Propylene", Nexant, 2009.
Chemsystems, "Vinyl Chloride Monomer (VCM0/Ethylene Dichloride (EDC) Perp 08-09-4", Nexant, Oct. 2009.
Choudhury, "Thermal Decomposition of t-Butyl Alcohol in Shock Waves", Combustion Scienve and Technology, 1990, vol. 71, iss 4-6, pp. 219-232.
Collins, "Disproportionation of Toulene over ZSM-5 under Near-Critical Conditions"AIChe Journal 1998, pp. 1211-1214, vol. 35, No. 7.
Davy Process Technology, "Butanediol and Co-Products", (1999).
Fernandez, "A Noise-Temperature Measurement System Using a Cryogenic Attenuator", TMO Progress Report 42-135, 1998.
Garner, "Asymmetric Multicomponent [C+NC+CC] Synthesis of Highly Functionalized Pyrrolidines Catalyzed by Silver(I)", Organic Letters, 2006, pp. 3647-3650, vol. 8, No. 17.
Gorman, "Soluble, Highly Conjugated Derivatives of Polyacetylene from the Ring-Opening Metathesis Polymerization of Monosubstituted Cyclooctatetraenes: Synthesis and the Relationship between Polymer Structure and Physical Properties", Office of Naval Research, Technical Report 1, prepared for J. Am. Chem. Soc, 1993, vol. 115, pp. 1397-1409.
Hanika, "Catalytic Transalkylation of Trimethylbenzenes with Toulene", Petroleum and Coal, 2003. pp. 78-82, vol. 45, 1-2.
Hendriksen, "Intermediates to Ethylene Glycol: Carbonylation of Formaldehyde Catalyzed by Nafion Solid Perfluorosulfonic Acid Resin", Exxon Research and Engineering Company, 1983.
Hoener, "The Production and Characterization of Mid-Gap States in trans-Polyacetylene", Thesis Ph.D, University of California, Berkeley, Aug. 1998.
ISIS.com, "Caprolactam Production and Manufacturing Process", Chemical Report, Apr. 23, 2010.
Jui, "Enantioselective Organo-SOMO Cycloadditions: A Catalytic Approach to Complex Pyrrolidines from Olefins and Aldehydes", J. Am. Chem. So., 2012, pp. 11400-11403, vol. 134.
Kolts, "Enhanced Ethylene and Ethane Production with Free-Radical Cracking Catalysts", Science, May 1986, pp. 744-746, vol. 32.
Kopke, "2,3-Butanediol Production by Acetrogenic Bacteria, an Alternative Route to Chemical Synthesis, Using Industrial Waste Gas", Applied and Environmental Microbiology, 2011, pp. 5467-5475, vol. 77, No. 15.
Lim, "Production of Ethylbenzene from Benzene and Ethylene by Liquid-phase Alkylation Using Zeolite Catalysts", SRI Consulting, PEP Process Module, Oct. 1999.
Marcu, "Oxidative dehydrogenation of isobutane over a titanium pyrophosphate catalyst", J. Serb. Chem. Soc., 2005, pp. 791-798, vol. 70, 6.
Biochemistry Forum, "Three kinds of methyl acrylate production methods", Nature Network, Feb. 21, 2011.
Rep, "Side chain alkylation of toluene with methanol over basic zeolites—novel production route towards styrene?", Thesis—University of Twente, 2002.
Tai, "Temperature-controlled phase-transfer catalysis for ethylene glycol production from cellulose", Chem. Commun., 2012, pp. 7052-7054, vol. 48.
Takemoto, "Synthesis of Styrenes through the Biocatalytic Decarboxylation of trans-Cinnamic Acids by Plant Cell Cultures", Chem. Pharm. Bull., 2001, pp. 639-641, vol. 49, 5.
Tallman, "Naptha cracking for light olefins production", PTQ, 2010 Q3, pp. 87-91.
Towfighi, "Steam Cracking of Naptha in Packed Bed Reactors", Ind. Eng. Chem. Res., 2002, pp. 1419-1424, vol. 41.
Wang, "Review of Directly Producing Light Olefins via CO Hydrogenation", Journal of Natural Gas Chemistry, 2003, pp. 10-16, vol. 12.
White, "Novel Multistep Process for Production on N-Methyl-2-Pyrrolidone from Renewable Resources", Pacific Northwest National Laboratory, 2005.
Zimmermann, "Ethylene", Ullmann's Encyclopedia of Industrial Chemistry, Jun. 2000.
Zuidhof, "The Beckmann rearrangement of cyclohexanone oxime to ☐-caprolactam in micromixers and microchannels", Technische Universiteit Eindhoven, 2010.
U.S. Appl. No. 13/947,485, filed Jul. 22, 2013, Negiz et al.
U.S. Appl. No. 13/947,404, filed Jul. 22, 2013, Stevens et al.
U.S. Appl. No. 13/950,763, filed Jul. 25, 2013, Rende et al.
U.S. Appl. No. 13/925,115, filed Jun. 24, 2013, Rende et al.
U.S. Appl. No. 13/950,526, filed Jul. 25, 2013, Rende et al.
U.S. Appl. No. 13/941,631, filed Jul. 15, 2013, Rende et al.
U.S. Appl. No. 13/950,921, filed Jul. 25, 2013, Rende et al.
U.S. Appl. No. 13/950,886, filed Jul. 25, 2013, Rende et al.
U.S. Appl. No. 13/950,504, filed Jul. 25, 2013, Rende et al.
U.S. Appl. No. 13/950,475, filed Jul. 25, 2013, Rende et al.
U.S. Appl. No. 13/941,620, filed Jul. 15, 2013, Rende et al.
U.S. Appl. No. 13/942,676, filed Jul. 15, 2013, Rende et al.
U.S. Appl. No. 13/943,848, filed Jul. 17, 2013, Rende et al.
U.S. Appl. No. 13/943,845, filed Jul. 17, 2013, Rende et al.
U.S. Appl. No. 13/943,840, filed Jul. 17, 2013, Rende et al.
U.S. Appl. No. 13/942,871, filed Jul. 16, 2013, Rende et al.
U.S. Appl. No. 13/943,852, filed Jul. 17, 2013, Rende et al.
U.S. Appl. No. 13/942,682, filed Jul. 15, 2013, Rende et al.
U.S. Appl. No. 13/950,830, filed Jul. 25, 2013, Rende et al.
U.S. Appl. No. 13/943,856, filed Jul. 17, 2013, Rende et al.
U.S. Appl. No. 13/950,787, filed Jul. 25, 2013, Rende et al.
U.S. Appl. No. 13/966,367, filed Aug. 14, 2013, Bricker et al.
U.S. Appl. No. 13/915,143, filed Jun. 11, 2013, Bricker et al.
U.S. Appl. No. 13/915,151, filed Jun. 11, 2013, Bricker et al.
U.S. Appl. No. 13/915,020, filed Jun. 11, 2013, Bricker et al.
U.S. Appl. No. 13/915,159, filed Jun. 11, 2013, Bricker et al.
U.S. Appl. No. 13/915,057, filed Jun. 11, 2013, Bricker et al.
U.S. Appl. No. 13/915,099, filed Jun. 11, 2013, Bricker et al.
U.S. Appl. No. 13/915,106, filed Jun. 11, 2013, Bricker et al.
U.S. Appl. No. 13/915,113, filed Jun. 11, 2013, Bricker et al.
U.S. Appl. No. 13/915,130, filed Jun. 11, 2013, Bricker et al.
U.S. Appl. No. 13/966,544, filed Aug. 14, 2013, Bricker et al.
U.S. Appl. No. 13/967,459, filed Aug. 15, 2013, Rende et al.
U.S. Appl. No. 13/952,810, filed Jul. 29, 2013, Rende et al.
U.S. Appl. No. 13/916,913, filed Jun. 13, 2013, Bedard et al.
U.S. Appl. No. 13/967,327, filed Aug. 14, 2013, Bedard et al.
U.S. Appl. No. 13/966,961, filed Aug. 14, 2013, Bedard et al.
U.S. Appl. No. 13/966,752, filed Aug. 14, 2013, Bedard et al.
U.S. Appl. No. 13/964,458, filed Aug. 12, 2013, Bedard et al.
U.S. Appl. No. 13/964,486, filed Aug. 12, 2013, Bedard et al.
U.S. Appl. No. 13/964,396, filed Aug. 12, 2013, Bedard et al.
U.S. Appl. No. 13/964,498, filed Aug. 12, 2013, Bedard et al.
U.S. Appl. No. 13/916,924, filed Jun. 13, 2013, Bedard et al.
U.S. Appl. No. 13/916,936, filed Jun. 13, 2013, Bedard et al.
U.S. Appl. No. 13/967,373, filed Aug. 15, 2013, Bedard et al.
U.S. Appl. No. 13/967,334, filed Aug. 14, 2013, Bedard et al.
U.S. Appl. No. 13/967,404, filed Aug. 15, 2013, Bedard et al.
U.S. Appl. No. 13/967,397, filed Aug. 15, 2013, Bedard et al.
U.S. Appl. No. 13/967,391, filed Aug. 15, 2013, Bedard et al.
U.S. Appl. No. 13/967,428, filed Aug. 15, 2013, Bedard et al.
U.S. Appl. No. 13/967,440, filed Aug. 15, 2013, Bedard et al.
U.S. Appl. No. 13/967,533, filed Aug. 15, 2013, Bedard et al.

(56) References Cited

OTHER PUBLICATIONS

U.S. Appl. No. 13/967,674, filed Aug. 15, 2013, Bedard et al.
U.S. Appl. No. 13/964,524, filed Aug. 12, 2013, Bedard et al.
U.S. Appl. No. 13/967,697, filed Aug. 15, 2013, Bedard et al.
U.S. Appl. No. 13/967,792, filed Aug. 15, 2013, Bedard et al.
U.S. Appl. No. 13/964,411, filed Aug. 12, 2013, Towler et al.
U.S. Appl. No. 13/964,425, filed Aug. 12, 2013, Towler et al.
U.S. Appl. No. 13/916,966, filed Jun. 13, 2013, Bedard et al.
U.S. Appl. No. 13/967,741, filed Aug. 15, 2013, Towler et al.
Smidt et al., "The Oxidation of Olefins with Palladium Chloride Catalysts", Angew. Chem. Internatio. Edit., 1962, pp. 80-88, vol. 1, No. 2.
U.S. Appl. No. 13/947,519, filed Jul. 22, 2013, Negiz et al.
Beskov, "Chemical Technology and the Fundamentals of Industrial Ecology: Textbook for Universities", Moscow, Khimiya, 1999, p. 182-184.
Fischer, "Self-repairing material systems—a dream or a reality?", Natural Science, vol. 2, No. 8, 873-901 (2010).
Froggatt, "Nuclear Power: Myth and Reality", Dec. 2005, No. 2, Russian version, p. 24.
Knunyantsa, "Soviet Encyclopedia", G.A. Jagodin Publishing, Moscow, 1988, vol. 1, col. 209.
Knunyantsa, "Soviet Encyclopedia", G.A. Jagodin Publishing, Moscow, 1990, vol. 2, col. 249-250.
Knunyantsa, "Great Russian Encyclopedia", Scientific Publishing, Moscow, 1992, vol. 3, col. 649-650.
Knunyantsa "Soviet Encyclopedia", G.A. Jagodin Publishing, Moscow, 1988, vol. 1, col. 931.
Lefevr, "Processes in Combustion Chambers", MIR, Moscow, 1986, p. 317-323.
Matar, "Chemistry of Petrochemical Processes" Second Edition, Provides Quick and Easy Access to Hundreds of Reactions, Processes and Products, 1994, 2000 by Gulf Publishing Company, Houston, Texas, p. 392, p. 214, last paragraph, p. 95, p. 94, Figs. 3-12, p. 246-248, p. 206, lines 8-11, p. 209-210, p. 247, paragraph 1, p. 205-206, p. 33-34, p. 91, paragraph 1.
Nikitin, book "Brief Guidelines of Gas Welder and Burner", 1960, p. 24.
Novoselov, "Electric Field Effect in Atomically Thin Carbon Films", Science 306, 666-669 (2004).
Reed, "The Superalloys: Fundamentals and Applications", Cambridge University Press, 2006, p. 1.
Shah, Ullmann's Encyclopedia of Industrial Chemistry, 2007, Heat Exchange, p. 14-17, 27, 31, 46-48.
Zolotova, "Great Russian Encyclopedia", Scientific Publishing, Moscow, 1992, vol. 3, col. 5-8.
Laukhuf, "Adsorption of Carbon Dioxide, Acetylene, Ethane, and Propylene on Charcoal at Near Room Temperatures", Journal of Chemical and Engineering Data, vol. 14, No. 1, Jan. 1969, p. 48-51.
Ren, "Olefins from conventional and heavy feedstocks: Energy use in steam cracking and alternative processes", Energy 31 (2006) 425-451.
Search Report dated Oct. 18, 2013 for corresponding PCT Appl. No. PCT/US2013/047450.

PRODUCTION OF OXYGENATES FROM A METHANE CONVERSION PROCESS

CROSS-REFERENCE TO RELATED APPLICATION

This application claims priority from Provisional Application No. 61/691,368 filed Aug. 21, 2012, the contents of which are hereby incorporated by reference in its entirety.

FIELD OF THE INVENTION

A process is disclosed for producing chemicals useful for the production of polymers from the conversion of methane to acetylene using a supersonic flow reactor. More particularly, the process is for the production of oxygenates.

BACKGROUND OF THE INVENTION

The use of plastics and rubbers are widespread in today's world. The production of these plastics and rubbers are from the polymerization of monomers which are generally produced from petroleum. The monomers are generated by the breakdown of larger molecules to smaller molecules which can be modified. The monomers are then reacted to generate larger molecules comprising chains of the monomers. An important example of these monomers are light olefins, including ethylene and propylene, which represent a large portion of the worldwide demand in the petrochemical industry. Light olefins, and other monomers, are used in the production of numerous chemical products via polymerization, oligomerization, alkylation and other well-known chemical reactions. Producing large quantities of light olefin material in an economical manner, therefore, is a focus in the petrochemical industry. These monomers are essential building blocks for the modern petrochemical and chemical industries. The main source for these materials in present day refining is the steam cracking of petroleum feeds.

A principal means of production is the cracking of hydrocarbons brought about by heating a feedstock material in a furnace has long been used to produce useful products, including for example, olefin products. For example, ethylene, which is among the more important products in the chemical industry, can be produced by the pyrolysis of feedstocks ranging from light paraffins, such as ethane and propane, to heavier fractions such as naphtha. Typically, the lighter feedstocks produce higher ethylene yields (50-55% for ethane compared to 25-30% for naphtha); however, the cost of the feedstock is more likely to determine which is used. Historically, naphtha cracking has provided the largest source of ethylene, followed by ethane and propane pyrolysis, cracking, or dehydrogenation. Due to the large demand for ethylene and other light olefinic materials, however, the cost of these traditional feeds has steadily increased.

Energy consumption is another cost factor impacting the pyrolytic production of chemical products from various feedstocks. Over the past several decades, there have been significant improvements in the efficiency of the pyrolysis process that have reduced the costs of production. In a typical or conventional pyrolysis plant, a feedstock passes through a plurality of heat exchanger tubes where it is heated externally to a pyrolysis temperature by the combustion products of fuel oil or natural gas and air. One of the more important steps taken to minimize production costs has been the reduction of the residence time for a feedstock in the heat exchanger tubes of a pyrolysis furnace. Reduction of the residence time increases the yield of the desired product while reducing the production of heavier by-products that tend to foul the pyrolysis tube walls. However, there is little room left to improve the residence times or overall energy consumption in tradition pyrolysis processes.

More recent attempts to decrease light olefin production costs include utilizing alternative processes and/or feedstreams. In one approach, hydrocarbon oxygenates and more specifically methanol or dimethylether (DME) are used as an alternative feedstock for producing light olefin products. Oxygenates can be produced from available materials such as coal, natural gas, recycled plastics, various carbon waste streams from industry and various products and by-products from the agricultural industry. Making methanol and other oxygenates from these types of raw materials is well established and typically includes one or more generally known processes such as the manufacture of synthesis gas using a nickel or cobalt catalyst in a steam reforming step followed by a methanol synthesis step at relatively high pressure using a copper-based catalyst.

Once the oxygenates are formed, the process includes catalytically converting the oxygenates, such as methanol, into the desired light olefin products in an oxygenate to olefin (OTO) process. Techniques for converting oxygenates, such as methanol to light olefins (MTO), are described in U.S. Pat. No. 4,387,263, which discloses a process that utilizes a catalytic conversion zone containing a zeolitic type catalyst. U.S. Pat. No. 4,587,373 discloses using a zeolitic catalyst like ZSM-5 for purposes of making light olefins. U.S. Pat. Nos. 5,095,163; 5,126,308 and 5,191,141 on the other hand, disclose an MTO conversion technology utilizing a non-zeolitic molecular sieve catalytic material, such as a metal aluminophosphate (ELAPO) molecular sieve. OTO and MTO processes, while useful, utilize an indirect process for forming a desired hydrocarbon product by first converting a feed to an oxygenate and subsequently converting the oxygenate to the hydrocarbon product. This indirect route of production is often associated with energy and cost penalties, often reducing the advantage gained by using a less expensive feed material. In addition, some oxygenates, such as vinyl acetate or acrylic acid, are also useful chemicals and can be used as polymer building blocks.

Recently, attempts have been made to use pyrolysis to convert natural gas to ethylene. U.S. Pat. No. 7,183,451 discloses heating natural gas to a temperature at which a fraction is converted to hydrogen and a hydrocarbon product such as acetylene or ethylene. The product stream is then quenched to stop further reaction and subsequently reacted in the presence of a catalyst to form liquids to be transported. The liquids ultimately produced include naphtha, gasoline, or diesel. While this method may be effective for converting a portion of natural gas to acetylene or ethylene, it is estimated that this approach will provide only about a 40% yield of acetylene from a methane feed stream. While it has been identified that higher temperatures in conjunction with short residence times can increase the yield, technical limitations prevent further improvement to this process in this regard.

While the foregoing traditional pyrolysis systems provide solutions for converting ethane and propane into other useful hydrocarbon products, they have proven either ineffective or uneconomical for converting methane into these other products, such as, for example ethylene. While MTO technology is promising, these processes can be expensive due to the indirect approach of forming the desired product. Due to continued increases in the price of feeds for traditional processes, such as ethane and naphtha, and the abundant supply and corresponding low cost of natural gas and other methane sources available, for example the more recent accessibility of shale gas, it is desirable to provide commercially feasible and cost effective ways to use methane as a feed for producing ethylene and other useful hydrocarbons.

SUMMARY

A method for producing acetylene according to one aspect is provided. The method generally includes introducing a feed stream portion of a hydrocarbon stream including methane into a supersonic reactor. The method also includes pyrolyzing the methane in the supersonic reactor to form a reactor effluent stream portion of the hydrocarbon stream including acetylene. The method further includes treating at least a portion of the hydrocarbon stream in a process for producing higher value products, and in particular oxygenates. There are many oxygenates that are important precursors for the production of polymers and other chemicals, among them aldehydes, alcohols and ethers.

The present invention includes a process for converting methane to oxygenates having 2 or more carbon atoms. The process includes passing methane to a supersonic reactor to covert the methane to acetylene through a pyrolysis reaction within the reactor. The acetylene is passed to a hydrogenation reactor to convert the acetylene to olefins, and in particular ethylene. The ethylene can be oligomerized to increase the carbon chain length of the olefin, and the olefins are passed to an aldehyde conversion reactor to generate an effluent stream comprising aldehydes.

In one embodiment, the process is for converting methane to alcohols having 2 or more carbon atoms. The acetylene stream can be reacted to convert to alcohols, or can be hydrogenated to generate an olefin stream comprising ethylene. The ethylene can be reacted with water to generate an alcohol in an alcohol conversion reactor, or can be passed to an oligomerization reactor to generate larger olefins, with the larger olefins passed to the alcohol conversion reactor, to generate an effluent stream comprising larger alcohols.

In yet another embodiment, the present invention includes a process for converting methane to ethers. The acetylene generated by the reactor can be passed to an etherization reactor to generate an effluent stream comprising ether compounds. The acetylene stream can optionally be processed to create larger ether compounds through hydrogenation and oligomerization of ethylene, or through polymerization of the acetylene.

Other objects, advantages and applications of the present invention will become apparent to those skilled in the art from the following detailed description and drawings.

DETAILED DESCRIPTION

Figure 1:
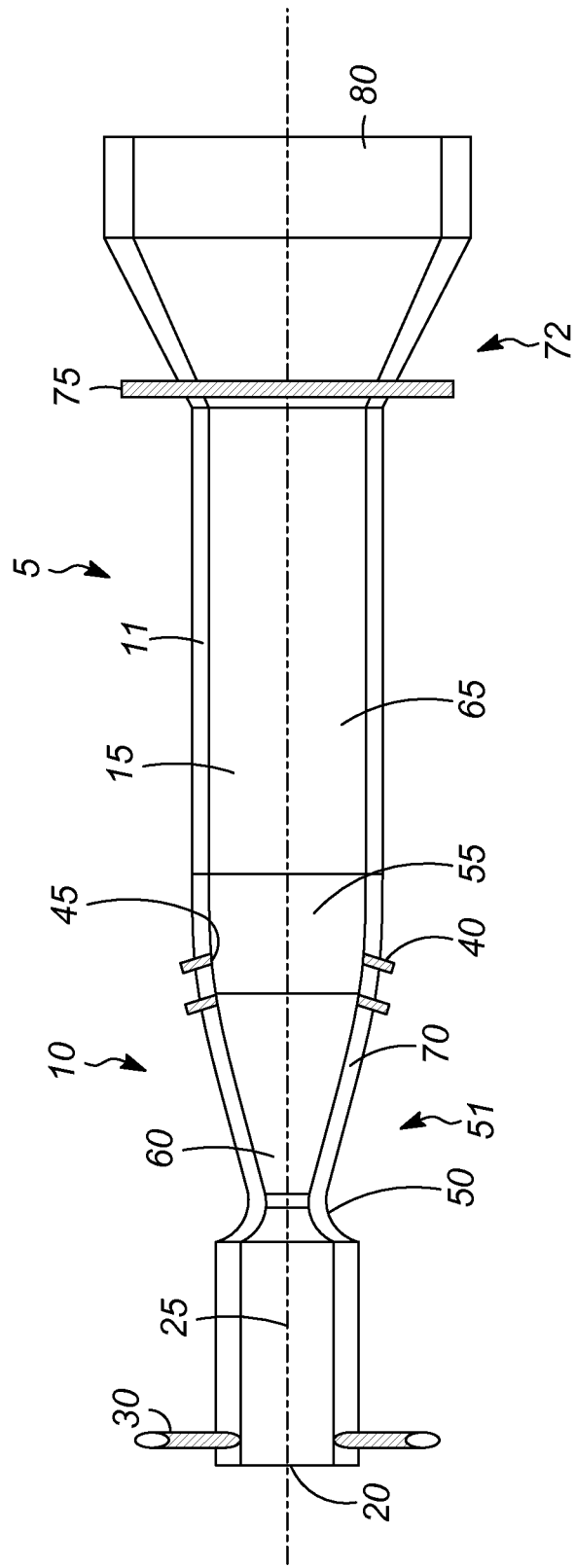
FIG. 1 is a side cross-sectional view of a supersonic reactor in accordance with various embodiments described herein.

One proposed alternative to the previous methods of producing hydrocarbon products that has not gained much commercial traction includes passing a hydrocarbon feedstock into a supersonic reactor and accelerating it to supersonic speed to provide kinetic energy that can be transformed into heat to enable an endothermic pyrolysis reaction to occur.

Variations of this process are set out in U.S. Pat. Nos. 4,136,015 and 4,724,272, and Russian Patent No. SU 392723A. These processes include combusting a feedstock or carrier fluid in an oxygen-rich environment to increase the temperature of the feed and accelerate the feed to supersonic speeds. A shock wave is created within the reactor to initiate pyrolysis or cracking of the feed. In particular, the hydrocarbon feed to the reactor comprises a methane feed. The methane feed is reacted to generate an intermediate process stream which is then further processed to generate a hydrocarbon product stream. Particular product streams of interest are high value oxygenates.

More recently, U.S. Pat. Nos. 5,219,530 and 5,300,216 have suggested a similar process that utilizes a shock wave reactor to provide kinetic energy for initiating pyrolysis of natural gas to produce acetylene. More particularly, this process includes passing steam through a heater section to become superheated and accelerated to a nearly supersonic speed. The heated fluid is conveyed to a nozzle which acts to expand the carrier fluid to a supersonic speed and lower temperature. An ethane feedstock is passed through a compressor and heater and injected by nozzles to mix with the supersonic carrier fluid to turbulently mix together at a Mach 2.8 speed and a temperature of about 427° C. The temperature in the mixing section remains low enough to restrict premature pyrolysis. The shockwave reactor includes a pyrolysis section with a gradually increasing cross-sectional area where a standing shock wave is formed by back pressure in the reactor due to flow restriction at the outlet. The shock wave rapidly decreases the speed of the fluid, correspondingly rapidly increasing the temperature of the mixture by converting the kinetic energy into heat. This immediately initiates pyrolysis of the ethane feedstock to convert it to other products. A quench heat exchanger then receives the pyrolized mixture to quench the pyrolysis reaction.

Methods and systems for converting hydrocarbon components in methane feed streams using a supersonic reactor are generally disclosed. As used herein, the term "methane feed stream" includes any feed stream comprising methane. The methane feed streams provided for processing in the supersonic reactor generally include methane and form at least a portion of a process stream that includes at least one contaminant. The methods and systems presented herein remove or convert the contaminant in the process stream and convert at least a portion of the methane to a desired product hydrocarbon compound to produce a product stream having a reduced contaminant level and a higher concentration of the product hydrocarbon compound relative to the feed stream. By one approach, a hydrocarbon stream portion of the process stream includes the contaminant and methods and systems presented herein remove or convert the contaminant in the hydrocarbon stream.

The term "hydrocarbon stream" as used herein refers to one or more streams that provide at least a portion of the methane feed stream entering the supersonic reactor as described herein or are produced from the supersonic reactor from the methane feed stream, regardless of whether further treatment or processing is conducted on such hydrocarbon stream. The "hydrocarbon stream" may include the methane feed stream, a supersonic reactor effluent stream, a desired product stream exiting a downstream hydrocarbon conversion process or any intermediate or by-product streams formed during the processes described herein. The hydrocarbon stream may be carried via a process stream line 115, which includes lines for carrying each of the portions of the process stream described above. The term "process stream" as used herein includes the "hydrocarbon stream" as described above, as well as it may include a carrier fluid stream, a fuel stream, an oxygen source stream, or any streams used in the systems and the processes described herein. The process stream may be carried via a process stream line 115, which includes lines for carrying each of the portions of the process stream described above.

Prior attempts to convert light paraffin or alkane feed streams, including ethane and propane feed streams, to other hydrocarbons using supersonic flow reactors have shown promise in providing higher yields of desired products from a particular feed stream than other more traditional pyrolysis systems. Specifically, the ability of these types of processes to provide very high reaction temperatures with very short associated residence times offers significant improvement over traditional pyrolysis processes. It has more recently been realized that these processes may also be able to convert methane to acetylene and other useful hydrocarbons, whereas more traditional pyrolysis processes were incapable or inefficient for such conversions.

The majority of previous work with supersonic reactor systems, however, has been theoretical or research based, and thus has not addressed problems associated with practicing the process on a commercial scale. In addition, many of these prior disclosures do not contemplate using supersonic reactors to effectuate pyrolysis of a methane feed stream, and tend to focus primarily on the pyrolysis of ethane and propane. One problem that has recently been identified with adopting the use of a supersonic flow reactor for light alkane pyrolysis, and more specifically the pyrolysis of methane feeds to form acetylene and other useful products therefrom, includes negative effects that particular contaminants in commercial feed streams can create on these processes and/or the products produced therefrom. Previous work has not considered the need for product purity, especially in light of potential downstream processing of the reactor effluent stream. Product purity can include the separation of several products into separate process streams, and can also include treatments for removal of contaminants that can affect a downstream reaction, and downstream equipment.

In accordance with various embodiments disclosed herein, therefore, processes and systems for converting the methane to a product stream are presented. The methane is converted to an intermediate process stream comprising acetylene. The intermediate process stream is converted to a second process stream comprising either a hydrocarbon product, or a second intermediate hydrocarbon compound. The processing of the intermediate acetylene stream can include purification or separation of acetylene from by-products.

The removal of particular contaminants and/or the conversion of contaminants into less deleterious compounds has been identified to improve the overall process for the pyrolysis of light alkane feeds, including methane feeds, to acetylene and other useful products. In some instances, removing these compounds from the hydrocarbon or process stream has been identified to improve the performance and functioning of the supersonic flow reactor and other equipment and processes within the system. Removing these contaminants from hydrocarbon or process streams has also been found to reduce poisoning of downstream catalysts and adsorbents used in the process to convert acetylene produced by the supersonic reactor into other useful hydrocarbons, for example hydrogenation catalysts that may be used to convert acetylene into ethylene. Still further, removing certain contaminants from a hydrocarbon or process stream as set forth herein may facilitate meeting product specifications.

In accordance with one approach, the processes and systems disclosed herein are used to treat a hydrocarbon process stream, to remove a contaminant therefrom and convert at least a portion of methane to acetylene. The hydrocarbon process stream described herein includes the methane feed stream provided to the system, which includes methane and may also include ethane or propane. The methane feed stream may also include combinations of methane, ethane, and propane at various concentrations and may also include other hydrocarbon compounds. In one approach, the hydrocarbon feed stream includes natural gas. The natural gas may be provided from a variety of sources including, but not limited to, gas fields, oil fields, coal fields, fracking of shale fields, biomass, and landfill gas. In another approach, the methane feed stream can include a stream from another portion of a refinery or processing plant. For example, light alkanes, including methane, are often separated during processing of crude oil into various products and a methane feed stream may be provided from one of these sources. These streams may be provided from the same refinery or different refinery or from a refinery off gas. The methane feed stream may include a stream from combinations of different sources as well.

In accordance with the processes and systems described herein, a methane feed stream may be provided from a remote location or at the location or locations of the systems and methods described herein. For example, while the methane feed stream source may be located at the same refinery or processing plant where the processes and systems are carried out, such as from production from another on-site hydrocarbon conversion process or a local natural gas field, the methane feed stream may be provided from a remote source via pipelines or other transportation methods. For example a feed stream may be provided from a remote hydrocarbon processing plant or refinery or a remote natural gas field, and provided as a feed to the systems and processes described herein. Initial processing of a methane stream may occur at the remote source to remove certain contaminants from the methane feed stream. Where such initial processing occurs, it may be considered part of the systems and processes described herein, or it may occur upstream of the systems and processes described herein. Thus, the methane feed stream provided for the systems and processes described herein may have varying levels of contaminants depending on whether initial processing occurs upstream thereof.

In one example, the methane feed stream has a methane content ranging from about 65 mol-% to about 100 mol-%. In another example, the concentration of methane in the hydrocarbon feed ranges from about 80 mol-% to about 100 mol-% of the hydrocarbon feed. In yet another example, the concentration of methane ranges from about 90 mol-% to about 100 mol-% of the hydrocarbon feed.

In one example, the concentration of ethane in the methane feed ranges from about 0 mol-% to about 35 mol-% and in another example from about 0 mol-% to about 10 mol-%. In one example, the concentration of propane in the methane feed ranges from about 0 mol-% to about 5 mol-% and in another example from about 0 mol-% to about 1 mol-%.

The methane feed stream may also include heavy hydrocarbons, such as aromatics, paraffinic, olefinic, and naphthenic hydrocarbons. These heavy hydrocarbons if present will likely be present at concentrations of between about 0 mol-% and about 100 mol-%. In another example, they may be present at concentrations of between about 0 mol-% and 10 mol-% and may be present at between about 0 mol-% and 2 mol-%.

In one embodiment, the present invention is a process for the production of aldehydes from methane. The method includes introducing a feed stream comprising methane into a supersonic reactor where the methane undergoes a pyrolysis reaction and is converted to an effluent stream having acetylene. In one aspect of the invention, the acetylene effluent stream can optionally be passed through an enrichment unit to generate an enriched acetylene stream and a waste stream having carbon monoxide and hydrogen. The effluent stream is passed to a hydrogenation reactor at hydrogenation reaction conditions to form a second effluent stream having olefins. The olefin effluent stream is passed to an aldehyde conversion reactor at aldehyde conversion reaction conditions to form an effluent stream comprising aldehydes. Aldehyde formation can be performed with the CO separated from the methane to acetylene conversion reactor through the hydroformylation of the olefins.

In one aspect of the invention, an oxygen rich stream, such as air, is passed to the aldehyde conversion reactor. The aldehyde conversion reactor includes a catalyst for converting the olefins to aldehydes. Conversion catalysts include metal chloride catalysts, where examples of preferred catalysts include palladium chloride (PdCl2) and copper chloride (CuCl2). Another aspect of the aldehyde conversion includes passing water, or steam, to the aldehyde conversion reactor. The reaction conditions include operating the reaction over the catalyst in a basis environment. The reaction conditions to obtain the basic environment can include adding an alkali compound, alkaline earth compound, or an amine compound.

One embodiment of the present invention includes converting methane to higher alcohols having 2 or more carbon atoms. The process includes converting the methane in the supersonic reactor to form a reactor effluent stream comprising acetylene, and reacting the acetylene in an alcohol conversion reactor at alcohol conversion reaction conditions to form an effluent stream comprising alcohols. The process further includes adding water to the alcohol conversion reactor, where the reaction is carried out over an acidic catalyst. Examples of acidic catalysts include zeolites, acidic non-zeolitic molecular sieves, acids, acidified refractory materials, acidic clays and mixtures thereof.

One aspect of this embodiment includes passing the acetylene stream to a hydrogenation reactor operated at hydrogenation reaction conditions to generate an effluent stream comprising ethylene. The ethylene stream is passed to an oligomerization reactor, or a dimerization reactor to increase the olefin chain length, and to generate an effluent stream comprising olefins having 3 or more carbon atoms. The olefin stream is passed to the alcohol conversion reactor to generate an effluent stream comprising alcohols.

In one embodiment, the process can further include a reactor for converting the alcohols to diols. Diols have numerous commercial uses, and include ethylene glycol, a common coolant, butanediols which are used for generating some polymers, and other diols such as dihydroxybenzene which is used in the pharmaceutical industry.

Hydrogenation reactors comprise a hydrogenation catalyst, and are operated at hydrogenation conditions to hydrogenate unsaturated hydrocarbons. Hydrogenation catalysts typically comprise a hydrogenation metal on a support, wherein the hydrogenation metal is preferably selected from a Group VIII metal in an amount between 0.01 and 2 wt. % of the catalyst. Preferably the metal is platinum (Pt), palladium (Pd), or a mixture thereof. The support is preferably a molecular sieve, and can include zeolites such as zeolite beta, MCM-22, MCM-36, mordenite, faujasites such as X-zeolites and Y-zeolites, including B-Y-zeolites and USY-zeolites; non-zeolitic solids such as silica-alumina, sulfated oxides such as sulfated oxides of zirconium, titanium, or tin, mixed oxides of zirconium, molybdenum, tungsten, phosphorus and chlorinated aluminium oxides or clays. Preferred supports are zeolites, including mordenite, zeolite beta, faujasites such as X-zeolites and Y-zeolites, including BY-zeolites and USY-zeolites. Mixtures of solid supports can also be employed.

In one embodiment, the present invention is for the production of ethers from methane. The methane is converted to acetylene through the pyrolysis reaction discussed above, and the effluent can be enriched to create an enriched acetylene stream. The acetylene is passed to an etherization reactor at etherization reaction conditions to form a second effluent stream comprising ethers. For larger ether compounds, the acetylene can be dimerized, polymerized, or passed through a hydrogenation reactor to convert to ethylene with the ethylene oligomerized to a desired carbon change length range. The etherization reaction is carried out in the presence of a base, including alkali compounds, alkaline earth compounds, and amine compounds.

The process for forming acetylene from the methane feed stream described herein utilizes a supersonic flow reactor for pyrolyzing methane in the feed stream to form acetylene. The supersonic flow reactor may include one or more reactors capable of creating a supersonic flow of a carrier fluid and the methane feed stream and expanding the carrier fluid to initiate the pyrolysis reaction. In one approach, the process may include a supersonic reactor as generally described in U.S. Pat. No. 4,724,272, which is incorporated herein by reference, in their entirety. In another approach, the process and system may include a supersonic reactor such as described as a "shock wave" reactor in U.S. Pat. Nos. 5,219,530 and 5,300,216, which are incorporated herein by reference, in their entirety. In yet another approach, the supersonic reactor described as a "shock wave" reactor may include a reactor such as described in "Supersonic Injection and Mixing in the Shock Wave Reactor" Robert G. Cerff, University of Washington Graduate School, 2010.

While a variety of supersonic reactors may be used in the present process, an exemplary reactor 5 is illustrated in FIG. 1. Referring to FIG. 1, the supersonic reactor 5 includes a reactor vessel 10 generally defining a reactor chamber 15. While the reactor 5 is illustrated as a single reactor, it should be understood that it may be formed modularly or as separate vessels. A combustion zone or chamber 25 is provided for combusting a fuel to produce a carrier fluid with the desired temperature and flowrate. The reactor 5 may optionally include a carrier fluid inlet 20 for introducing a supplemental carrier fluid into the reactor. One or more fuel injectors 30 are provided for injecting a combustible fuel, for example hydrogen, into the combustion chamber 25. The same or other injectors may be provided for injecting an oxygen source into the combustion chamber 25 to facilitate combustion of the fuel. The fuel and oxygen are combusted to produce a hot carrier fluid stream typically having a temperature of from about 1200° C. to about 3500° C. in one example, between about 2000° C. and about 3500° C. in another example, and between about 2500° C. and 3200° C. in yet another example. According to one example the carrier fluid stream has a pressure of about 100 kPa or higher, greater than about 200 kPa in another example, and greater than about 400 kPa in another example.

The hot carrier fluid stream from the combustion zone 25 is passed through a converging-diverging nozzle 50 to accelerate the flowrate of the carrier fluid to above about mach 1.0 in one example, between about mach 1.0 and mach 4.0 in another example, and between about mach 1.5 and 3.5 in another example. In this regard, the residence time of the fluid in the reactor portion of the supersonic flow reactor is between about 0.5 to 100 ms in one example, about 1 to 50 ms in another example, and about 1.5 to 20 ms in another example.

A feedstock inlet 40 is provided for injecting the methane feed stream into the reactor 5 to mix with the carrier fluid. The feedstock inlet 40 may include one or more injectors 45 for injecting the feedstock into the nozzle 50, a mixing zone 55, an expansion zone 60, or a reaction zone or chamber 65. The injector 45 may include a manifold, including for example a plurality of injection ports.

In one approach, the reactor 5 may include a mixing zone 55 for mixing of the carrier fluid and the feed stream. In another approach, no mixing zone is provided, and mixing may occur in the nozzle 50, expansion zone 60, or reaction zone 65 of the reactor 5. An expansion zone 60 includes a diverging wall 70 to produce a rapid reduction in the velocity of the gases flowing therethrough, to convert the kinetic energy of the flowing fluid to thermal energy to further heat the stream to cause pyrolysis of the methane in the feed, which may occur in the expansion section 60 and/or a downstream reaction section 65 of the reactor. The fluid is quickly quenched in a quench zone 72 to stop the pyrolysis reaction from further conversion of the desired acetylene product to other compounds. Spray bars 75 may be used to introduce a quenching fluid, for example water or steam into the quench zone 72.

The reactor effluent exits the reactor via outlet 80 and as mentioned above forms a portion of the hydrocarbon stream. The effluent will include a larger concentration of acetylene than the feed stream and a reduced concentration of methane relative to the feed stream. The reactor effluent stream may also be referred to herein as an acetylene stream as it includes an increased concentration of acetylene. The acetylene may be an intermediate stream in a process to form another hydrocarbon product or it may be further processed and captured as an acetylene product stream. In one example, the reactor effluent stream has an acetylene concentration prior to the addition of quenching fluids ranging from about 2 mol-% to about 30 mol-%. In another example, the concentration of acetylene ranges from about 5 mol-% to about 25 mol-% and from about 8 mol-% to about 23 mol-% in another example.

In one example, the reactor effluent stream has a reduced methane content relative to the methane feed stream ranging from about 15 mol-% to about 95 mol-%. In another example, the concentration of methane ranges from about 40 mol-% to about 90 mol-% and from about 45 mol-% to about 85 mol-% in another example.

In one example the yield of acetylene produced from methane in the feed in the supersonic reactor is between about 40% and about 95%. In another example, the yield of acetylene produced from methane in the feed stream is between about 50% and about 90%. Advantageously, this provides a better yield than the estimated 40% yield achieved from previous, more traditional, pyrolysis approaches.

The invention can include an acetylene enrichment unit having an inlet in fluid communication with the reactor outlet, and an outlet for a acetylene enriched effluent. One aspect of the system can further include a contaminant removal zone having an inlet in fluid communication with the acetylene enrichment zone outlet, and an outlet in fluid communication with the hydrocarbon conversion zone inlet, for removing contaminants that can adversely affect downstream catalysts and processes. One contaminant to be removed is CO to a level of less than 0.1 mole %, and preferably to a level of less than 100 ppm by vol. An additional aspect of the invention is where the system can include a second contaminant removal zone having an inlet in fluid communication with the methane feed stream and an outlet in fluid communication with the supersonic reactor inlet.

By one approach, the reactor effluent stream is reacted to form another hydrocarbon compound. In this regard, the reactor effluent portion of the hydrocarbon stream may be passed from the reactor outlet to a downstream hydrocarbon conversion process for further processing of the stream. While it should be understood that the reactor effluent stream may undergo several intermediate process steps, such as, for example, water removal, adsorption, and/or absorption to provide a concentrated acetylene stream, these intermediate steps will not be described in detail herein.

Figure 2:
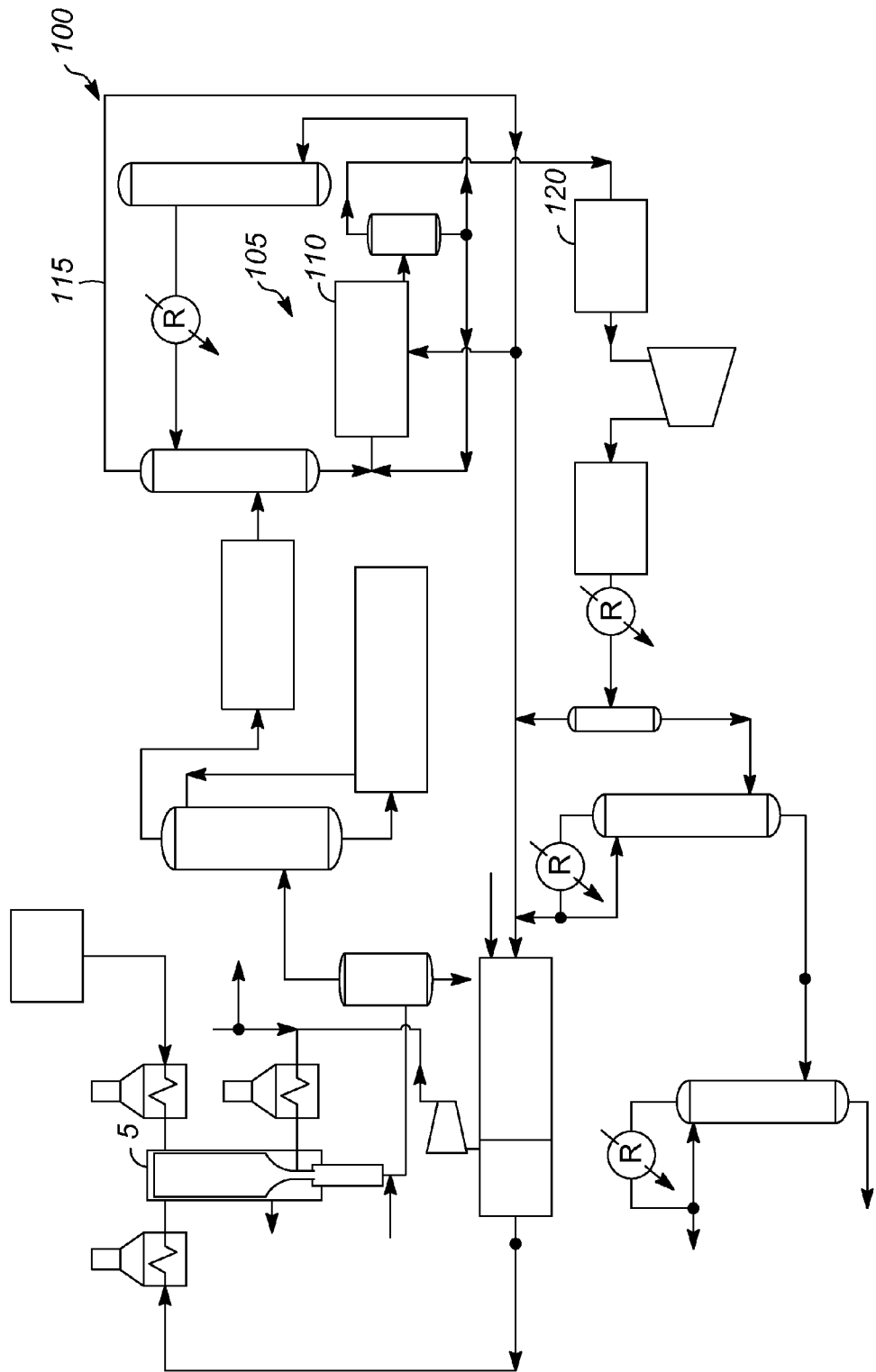
FIG. 2 is a schematic view of a system for converting methane into acetylene and other hydrocarbon products in accordance with various embodiments described herein.

Referring to FIG. 2, the reactor effluent stream having a higher concentration of acetylene may be passed to a downstream hydrocarbon conversion zone 100 where the acetylene may be converted to form another hydrocarbon product. The hydrocarbon conversion zone 100 may include a hydrocarbon conversion reactor 105 for converting the acetylene to another hydrocarbon product. While FIG. 2 illustrates a process flow diagram for converting at least a portion of the acetylene in the effluent stream to ethylene through hydrogenation in hydrogenation reactor 110, it should be understood that the hydrocarbon conversion zone 100 may include a variety of other hydrocarbon conversion processes instead of or in addition to a hydrogenation reactor 110, or a combination of hydrocarbon conversion processes. Similarly, it illustrated in FIG. 2 may be modified or removed and are shown for illustrative purposes and not intended to be limiting of the processes and systems described herein. Specifically, it has been identified that several other hydrocarbon conversion processes, other than those disclosed in previous approaches, may be positioned downstream of the supersonic reactor 5, including processes to convert the acetylene into other hydrocarbons, including, but not limited to: alkenes, alkanes, methane, acrolein, acrylic acid, acrylates, acrylamide, aldehydes, polyacetylides, benzene, toluene, styrene, aniline, cyclohexanone, caprolactam, propylene, butadiene, butyne diol, butandiol, C2-C4 hydrocarbon compounds, ethylene glycol, diesel fuel, diacids, diols, pyrrolidines, and pyrrolidones.

A contaminant removal zone 120 for removing one or more contaminants from the hydrocarbon or process stream may be located at various positions along the hydrocarbon or process stream depending on the impact of the particular contaminant on the product or process and the reason for the contaminants removal, as described further below. For example, particular contaminants have been identified to interfere with the operation of the supersonic flow reactor 5 and/or to foul components in the supersonic flow reactor 5. Thus, according to one approach, a contaminant removal zone is positioned upstream of the supersonic flow reactor in order to remove these contaminants from the methane feed stream prior to introducing the stream into the supersonic reactor. Other contaminants have been identified to interfere with a downstream processing step or hydrocarbon conversion process, in which case the contaminant removal zone may be positioned upstream of the supersonic reactor or between the supersonic reactor and the particular downstream processing step at issue. Still other contaminants have been identified that should be removed to meet particular product specifications. Where it is desired to remove multiple contaminants from the hydrocarbon or process stream, various contaminant removal zones may be positioned at different locations along the hydrocarbon or process stream. In still other approaches, a contaminant removal zone may overlap or be integrated with another process within the system, in which case the contaminant may be removed during another portion of the process, including, but not limited to the supersonic reactor 5 or the downstream hydrocarbon conversion zone 100. This may be accomplished with or without modification to these particular zones, reactors or processes. While the contaminant removal zone 120 illustrated in FIG. 2 is shown positioned downstream of the hydrocarbon conversion reactor 105, it should be understood that the contaminant removal zone 120 in accordance herewith may be positioned upstream of the supersonic flow reactor 5, between the supersonic flow reactor 5 and the hydrocarbon conversion zone 100, or downstream of the hydrocarbon conversion zone 100 as illustrated in FIG. 2 or along other streams within the process stream, such as, for example, a carrier fluid stream, a fuel stream, an oxygen source stream, or any streams used in the systems and the processes described herein.

While there have been illustrated and described particular embodiments and aspects, it will be appreciated that numerous changes and modifications will occur to those skilled in the art, and it is intended in the appended claims to cover all those changes and modifications which fall within the true spirit and scope of the present disclosure and appended claims.

The invention claimed is:

1. A method for producing aldehydes comprising:
   introducing a feed stream comprising methane into a supersonic reactor;
   converting the methane in the supersonic reactor to form a reactor effluent stream comprising acetylene;
   passing the reactor effluent stream to a hydrogenation reactor at hydrogenation reaction conditions to form a second effluent stream comprising olefins; and
   passing the second effluent stream to an aldehyde conversion reactor at aldehyde conversion reaction conditions to form an effluent stream comprising aldehydes.

2. The method of claim 1 further comprising:
   passing the second effluent stream to an oligomerization reactor to generate an oligomerization effluent stream; and
   passing the oligomerization effluent stream to the aldehyde conversion reactor, to generate an effluent stream comprising C4+ aldehydes.

3. The method of claim 1 further comprising passing an oxygen stream comprising oxygen to the aldehyde conversion reactor.

4. The method of claim 1 wherein the aldehyde reaction conditions include an aldehyde conversion catalyst.

5. The method of claim 4 wherein the oxidation catalyst is a metal chloride.

6. The method of claim 1 further comprising passing a second stream comprising water to the aldehyde conversion reactor.

7. The method of claim 6 wherein the aldehyde conversion reaction conditions include basic reaction conditions over a catalyst.

8. The method of claim 6 wherein in the basic reaction conditions include the addition of an alkali compound.

9. The method of claim 1 wherein the conversion reaction in the supersonic reactor is a pyrolysis reaction.

10. A method for producing alcohols comprising:
    introducing a feed stream comprising methane into a supersonic reactor;
    converting the methane in the supersonic reactor to form a reactor effluent stream comprising acetylene;
    passing the reactor effluent stream to a hydrogenation reactor at hydrogenation reaction conditions to form a second effluent stream comprising olefins; and
    passing the second effluent stream to an alcohol conversion reactor at alcohol conversion reaction conditions to form an effluent stream comprising alcohols.

11. The method of claim 10 further comprising passing water to the alcohol conversion reactor.

12. The method of claim 10 wherein the alcohol conversion reaction conditions include reacting over an acidic catalyst.

13. The method of claim 10 wherein the conversion reaction in the supersonic reactor is a pyrolysis reaction.

14. A method for producing alcohols comprising:
    introducing a feed stream comprising methane into a supersonic reactor;
    converting the methane in the supersonic reactor to form a reactor effluent stream comprising acetylene;
    passing the reactor effluent stream to a hydrogenation reactor at hydrogenation reaction conditions to form a second effluent stream comprising olefins; and
    passing the second effluent stream to an alcohol conversion reactor at alcohol conversion reaction conditions to form an effluent stream comprising alcohols.

15. The method of claim 14 further comprising:
    passing the second effluent stream to an oligomerization reactor to generate an oligomerization effluent stream; and
    passing the oligomerization effluent stream to the alcohol conversion reactor, to generate an effluent stream comprising C3+ alcohols.

16. The method of claim 14 further comprising passing a second stream comprising water to the alcohol conversion reactor.

17. The method of claim 14 wherein the alcohol conversion reaction conditions include an acidic catalyst.

18. The method of claim 17 wherein the acidic catalyst is selected from the group consisting of zeolites, acidic non-zeolitic molecular sieves, acids, acidified refractory materials, acidic clays and mixtures thereof.

19. The method of claim 14 further comprising passing the alcohol effluent stream to a third reactor for generating a third effluent stream comprising diols.

20. The method of claim 14 wherein the conversion reaction in the supersonic reactor is a pyrolysis reaction.

21. A method for producing ethers comprising:
    introducing a feed stream comprising methane into a supersonic reactor;
    converting the methane in the supersonic reactor to form a reactor effluent stream comprising acetylene;
    passing the reactor effluent stream to a hydrogenation reactor at hydrogenation reaction conditions to form a second effluent stream comprising olefins; and
    passing the second effluent stream to an etherization reactor at etherization reaction conditions to form a second effluent stream comprising ethers.

22. The method of claim 21 wherein the etherization conditions include the presence of a base.

23. The method of claim 21 further comprising passing a second stream comprising an alcohol to the etherization reactor.

24. The method of claim 21 wherein the conversion reaction in the supersonic reactor is a pyrolysis reaction.

* * * * *